(12) United States Patent
Smith et al.

(10) Patent No.: US 12,186,506 B2
(45) Date of Patent: Jan. 7, 2025

(54) MEDICAL DELIVERY DEVICE AND METHOD OF USE

(71) Applicant: Boston Scientific Scimed, Inc., Maple Grove, MN (US)

(72) Inventors: Amanda Smith, Boston, MA (US); Jennifer Mague, Marlborough, MA (US); Lauren Lydecker, Millbury, MA (US); Andrew Pic, Northboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 533 days.

(21) Appl. No.: 17/103,449

(22) Filed: Nov. 24, 2020

(65) Prior Publication Data

US 2021/0162185 A1    Jun. 3, 2021

Related U.S. Application Data

(60) Provisional application No. 62/942,925, filed on Dec. 3, 2019.

(51) Int. Cl.
*A61M 25/10* (2013.01)

(52) U.S. Cl.
CPC ....... *A61M 25/10* (2013.01); *A61M 2025/105* (2013.01); *A61M 2025/1081* (2013.01); *A61M 2025/1086* (2013.01); *A61M 2205/0238* (2013.01); *A61M 2205/3368* (2013.01)

(58) Field of Classification Search
CPC ....... A61M 2025/105; A61M 25/1018–10186; A61M 25/10; A61M 2205/0238; A61M 2205/3368; A61M 25/1002; A61B 17/0057; A61B 2017/0034; A61B 2017/00495; A61B 2017/0065; A61B 17/0049; A61B 17/12136; A61B 1/00082; A61B 1/015
See application file for complete search history.

(56) References Cited

U.S. PATENT DOCUMENTS

| | | | | |
|---|---|---|---|---|
| 3,860,007 A | * | 1/1975 | Binard | A61M 25/10185 604/920 |
| 4,417,576 A | * | 11/1983 | Baran | A61M 16/0481 604/101.02 |
| 4,423,725 A | * | 1/1984 | Baran | A61B 17/22 604/101.02 |

(Continued)

FOREIGN PATENT DOCUMENTS

| | | |
|---|---|---|
| EP | 1079872 B1 | 3/2001 |
| EP | 2328650 B1 | 6/2011 |

(Continued)

*Primary Examiner* — Theodore J Stigell
(74) *Attorney, Agent, or Firm* — Bookoff McAndrews, PLLC

(57) ABSTRACT

A medical device includes a sheath having a proximal end, a distal end, and at least one lumen extending from the proximal end to the distal end, and a balloon at the distal end of the sheath and having an inflated configuration and a deflated configuration. The balloon defines at least one space radially inward of an exterior surface of the balloon, the at least one space configured to retain a material, and the transition of the balloon from the deflated configuration to the inflated configuration delivers the material from the at least one space to a target site in a body.

17 Claims, 7 Drawing Sheets

(56) References Cited

U.S. PATENT DOCUMENTS

| | | | | |
|---|---|---|---|---|
| 4,994,033 A | * | 2/1991 | Shockey | A61M 16/0481 604/101.02 |
| 4,994,072 A | * | 2/1991 | Bhate | A61M 25/1038 604/917 |
| 5,049,132 A | * | 9/1991 | Shaffer | A61M 16/0456 604/101.02 |
| 5,232,444 A | * | 8/1993 | Just | A61M 25/104 604/218 |
| 6,543,446 B1 | * | 4/2003 | Christopher | A61M 16/0488 128/207.14 |
| 2011/0060275 A1 | | 3/2011 | Christiansen | |
| 2012/0283636 A1 | | 11/2012 | Rizq et al. | |
| 2014/0155824 A1 | | 6/2014 | Papp | |

FOREIGN PATENT DOCUMENTS

| | | |
|---|---|---|
| JP | H09192231 A | 7/1997 |
| JP | 2011513004 A | 4/2011 |
| WO | 2019131661 A1 | 7/2019 |

* cited by examiner

MEDICAL DELIVERY DEVICE AND METHOD OF USE

CROSS-REFERENCE TO RELATED APPLICATIONS

This application claims the benefit of priority from U.S. Provisional Application No. 62/942,925, filed on Dec. 3, 2019, which is incorporated by reference herein in its entirety.

TECHNICAL FIELD

The present disclosure relates generally to endoscopic medical devices and related methods of use. More particularly, in some embodiments, the disclosure relates to endoscopic medical tools and methods related to accessing target sites and dispensing materials to the target sites.

BACKGROUND

In certain medical procedures, it may be necessary to stop or minimize bleeding and/or supply therapeutic materials internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site and/or promote natural tissue healing, a hemostatic or regenerative agent or tissue adhesive may be delivered by a device inserted into the working channel of the endoscope. Agent/adhesive delivery may be achieved through mechanical systems, for example. Such systems, however, may not achieve a desired rate of agent delivery or a desired dosage of agent, may result in inconsistent dosing of agent, or may not result in the agent reaching the treatment site deep within the GI tract. The current disclosure may solve one or more of these issues or other issues in the art.

SUMMARY OF THE DISCLOSURE

According to an aspect, a medical device includes a sheath having a proximal end, a distal end, and at least one lumen extending from the proximal end to the distal end, and a balloon at the distal end of the sheath and having an inflated configuration and a deflated configuration. The balloon defines at least one space radially inward of an exterior surface of the balloon, the at least one space configured to retain a material, and the transition of the balloon from the deflated configuration to the inflated configuration delivers the material from the at least one space to a target site in a body.

The at least one lumen may include a sheath lumen, wherein the medical device may be configured to be attached to a fluid containment device, and wherein a fluid from the fluid containment device may be configured to be supplied to the sheath lumen to transition the balloon from the deflated configuration to the inflated configuration.

The at least one lumen ma include a delivery lumen defined by an outer wall of the balloon and an inner wall of the balloon, wherein the at least one space may include channels extending from respective openings in the outer wall and fluidly coupled to the delivery lumen, and wherein the delivery lumen may be fluidly decoupled from the sheath lumen.

The at least one space may include a balloon lumen disposed between an inner wall and an outer wall of the balloon, and wherein the balloon may include a plurality of openings in the outer wall of the balloon fluidly coupled to the balloon lumen.

Transition of the balloon from the deflated configuration to the inflated configuration may open the plurality of openings.

The balloon lumen and the sheath lumen may be separated by the inner wall, wherein the inner wall may include openings, and wherein transition of the balloon from the deflated configuration to the inflated configuration may open the openings in the inner wall to fluidly couple the sheath lumen to the balloon lumen.

The material may be configured to be disposed within the balloon lumen, and wherein transition of the balloon from the deflated configuration to the inflated configuration may cause the fluid to flow through the openings in the inner wall and mix with the material, and may deliver the material from the balloon lumen to the target site.

The plurality of openings in the outer wall of the balloon may be sealed in the deflated configuration by a perforated membrane.

The balloon may include folds in at least the deflated configuration, and the at least one space may be at least partially defined by the folds, and wherein at least one delineation of each of the folds may decrease in the inflated configuration to expose the at least one space to an external environment.

The at least one lumen may include an outer lumen disposed about the sheath lumen, wherein the outer lumen may extend from the proximal end of the sheath and terminates proximal of the balloon, and wherein an outer wall of the sheath may include sheath openings adjacent the balloon and fluidly coupled to the outer lumen.

The balloon may not include an outer coating of the material in the deflated configuration.

The at least one space may include channels extending from an outer surface of the balloon toward a central longitudinal axis of the balloon, and wherein each of the channels may include an opening at an outer surface of the balloon.

The material may be disposed within the channels in the deflated configuration, wherein each of the openings may be closed from an external environment in the deflated configuration to retain the material, and wherein transition from the deflated configuration to the inflated configuration may release the material from each of the channels through the openings.

The at least one lumen may include a delivery lumen defined by an outer wall of the balloon and an inner wall of the balloon, wherein the at least one space may include channels extending from an outer surface of the balloon toward a central longitudinal axis of the balloon, wherein each of the channels may include an opening at an outer surface of the balloon, and wherein the channels and the openings may be fluidly coupled to the delivery lumen.

A proximal end of the delivery lumen may be configured to be attached to a device containing the material, wherein the material may be configured to be delivered to a target site via the second lumen and the openings, and wherein the delivery lumen may be fluidly decoupled from any other lumen from the at least one lumen.

According to another aspect, a medical device includes a sheath having a proximal end, a distal end, and at least one lumen extending from the proximal end to the distal end, a balloon at the distal end of the sheath and having an inflated configuration and a deflated configuration, and a patch disposed on the balloon, wherein a material is provided on a first surface of the patch opposite a second surface of the patch facing the balloon, and wherein the material is configured to be delivered to a target site.

The patch may include an adhesive on the second surface of the patch which may be configured to maintain a position of the patch relative to the balloon, wherein a fluid may be configured to be supplied to the balloon via the at least one lumen to inflate the balloon to the inflated configuration, and wherein the fluid may be configured to change a temperature of the balloon to overcome an adhesion force of the adhesive between the patch and the balloon.

The at least one lumen may include a sheath lumen configured to receive a first fluid to inflate the balloon from the deflated configuration to the inflated configuration, and an outer lumen disposed about the sheath lumen, wherein the outer lumen may extend from the proximal end of the sheath and may terminate proximal of the balloon, wherein an outer surface of the sheath may include openings fluidly coupled to the outer lumen, and wherein a second fluid may be configured to be delivered to the second surface of the patch via the openings to overcome an adhesion force of the adhesive between the patch and the balloon.

According to yet another aspect, a method of performing a medical procedure includes positioning a sheath adjacent a target site within a body, supplying a fluid to a sheath lumen of the sheath to transition a balloon at the distal end of the sheath from a deflated configuration to an inflated configuration, supplying a material from the balloon to the target site as the balloon transitions from the deflated configuration to the inflated configuration from at least one space radially inward of an exterior surface of the balloon, and withdrawing the fluid from the sheath lumen to collapse the balloon from the inflated configuration to the deflated configuration.

The method may further include delivering a second fluid to the target site via an outer lumen about the sheath lumen, wherein the second fluid is configured to activate the material such that the material adheres to the target site.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
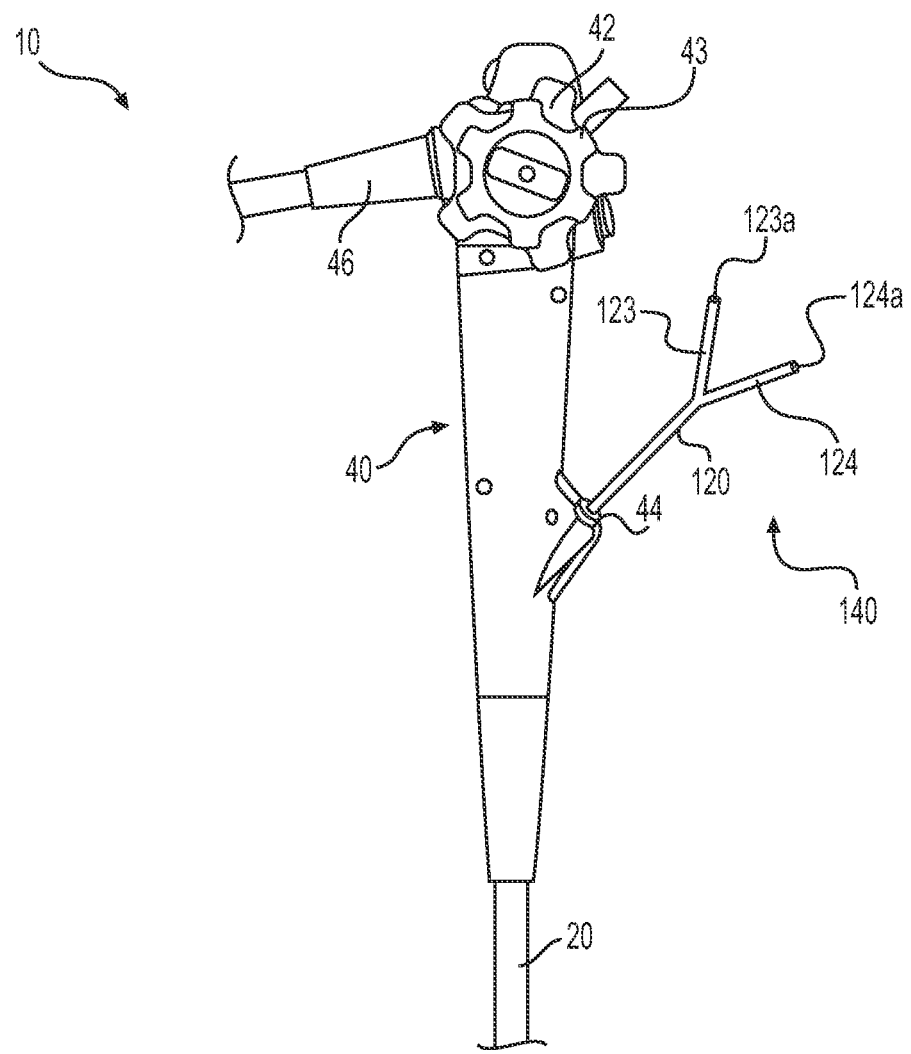
FIG. 1 is a perspective view of a medical system according to an embodiment.
Figure 1:
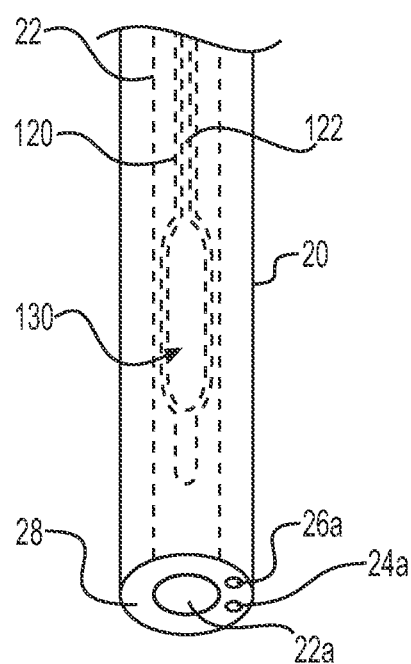

The present disclosure is now described with reference to an exemplary medical system that may be used to dispense materials endoscopically. However, it should be noted that reference to this particular procedure is provided only for convenience and not intended to limit the disclosure. A person of ordinary skill in the art would recognize that the concepts underlying the disclosed devices and application methods may be utilized in any suitable procedure, medical or otherwise. The present disclosure may be understood with reference to the following description and the appended drawings, wherein like elements are referred to with the same reference numerals.

For ease of description, the term "distal" refers to a portion farthest away from a user when introducing the system into a patient. By contrast, the term "proximal" refers to a portion closest to the user when introducing the system into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." In this disclosure, relative terms, such as, for example, "about," "substantially," "generally," and "approximately" are used to indicate a possible variation of ±10% in a stated value or characteristic.

Referring to FIG. 1, a medical system 10 according to an embodiment is shown. Medical system 10 includes a flexible shaft 20 (e.g., a catheter) and a handle 40 connected at a proximal end of flexible shaft 20. Handle 40, or some other device for actuating or controlling medical system 10 and any tool or devices associated with medical system 10, includes first and second actuating devices 42, 43. Devices 42, 43 control articulation of flexible shaft 20 and/or an articulation joint at a distal end of flexible shaft 20, in multiple directions. Devices 42, 43, may be, for example, rotatable knobs that rotate about their axes to push/pull actuating elements (not shown). The actuating elements, such as cables or wires suitable for medical procedures (e.g., medical grade plastic or metal), extend distally from a proximal end of endoscope 10 and connect to flexible shaft 20 to control movement thereof. Alternatively, or additionally, a user may operate actuating elements independently of handle 40. Distal ends of actuating elements extend through flexible shaft 20 and terminate at an articulation joint and/or a distal tip of flexible shaft 20. For example, one or more actuating elements may be connected to an articulation joint, and actuation of actuating elements may control the articulation joint or the distal end of flexible shaft 20 to move in multiple directions.

In addition, one or more electrical cables (not shown) may extend from the proximal end of endoscope 10 to the distal end of flexible shaft 20 and may provide electrical controls to imaging, lighting, and/or other electrical devices at the distal end of flexible shaft 20, and may carry imaging signals from the distal end of flexible shaft 20 proximally to be processed and/or displayed on a display. Handle 40 may also include ports 44, 46 for introducing and/or removing tools, fluids, or other materials from the patient. Port 44 may be used to introduce tools. Port 46 may be connected to an umbilicus for introducing fluid, suction, and/or wiring for electronic components. For example, as shown in FIG. 1, port 44 is connected to a lumen 22, which extends from the proximal end to the distal end of flexible shaft 20. Port 44 may receive a medical device, such as flexible sheath 120 (e.g., a catheter) of a medical device.

As shown in FIG. 1, sheath 120 may include a lumen 122 extending therethrough, from a proximal end to a distal end of sheath 120. Sheath 120 may incorporate, or otherwise be attached to, a distal end of an actuating device 140. Actuating device 140 is a Y-shaped member having a first channel 123 having a first opening 123a and a second channel 124 having a second opening 124a. As will be explained herein, first and second channels 123, 124 may communicate with lumen 122 and may be used for inflating or deflating a balloon 130 at a distal end of sheath 120. For example, attaching first channel 123 to a containment device (not shown) having a fluid F, and supplying fluid F (shown, e.g., by an arrow in FIG. 2A) to first channel 123 may inflate balloon 130, while attaching second channel 124 to the container may withdraw fluid F from balloon 130 and into the containment device, thereby deflating balloon 130. It will be understood that actuating device 140 is not limited to two channels. For example, additional channels may be included in actuating device 140 to provide additional fluid and/or materials to a distal end of sheath 120, as will be described herein. As a further example, actuating device 140 may include only a single channel for selectively introducing or removing materials, including fluids, to or from lumen 122.

Figure 2A:
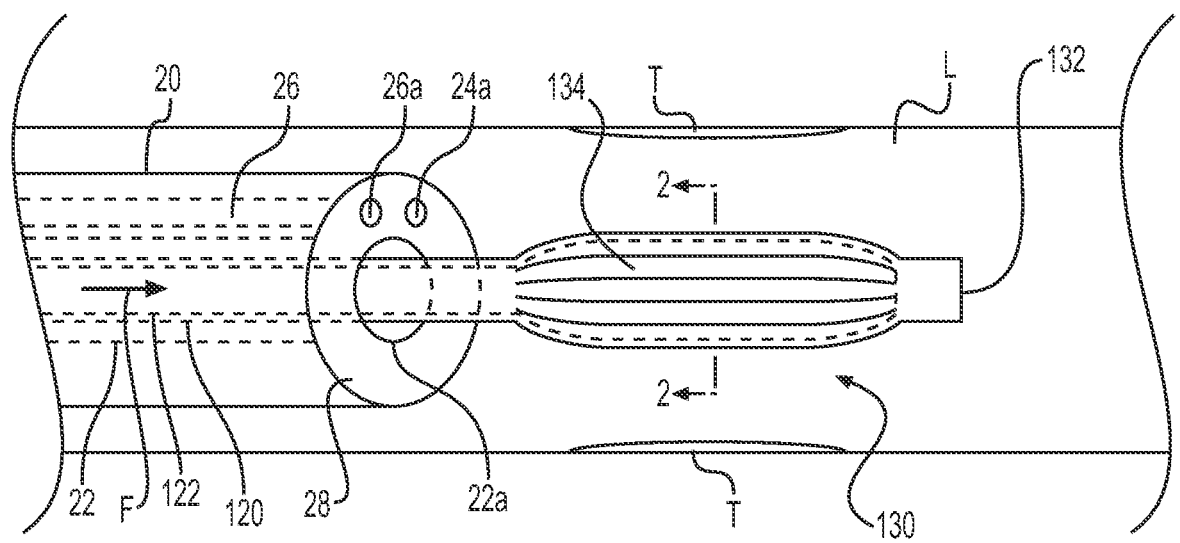
FIG. 2A is a perspective view of a distal end of a medical tool of the medical system of FIG. 1, according to an embodiment.
Figure 3A:
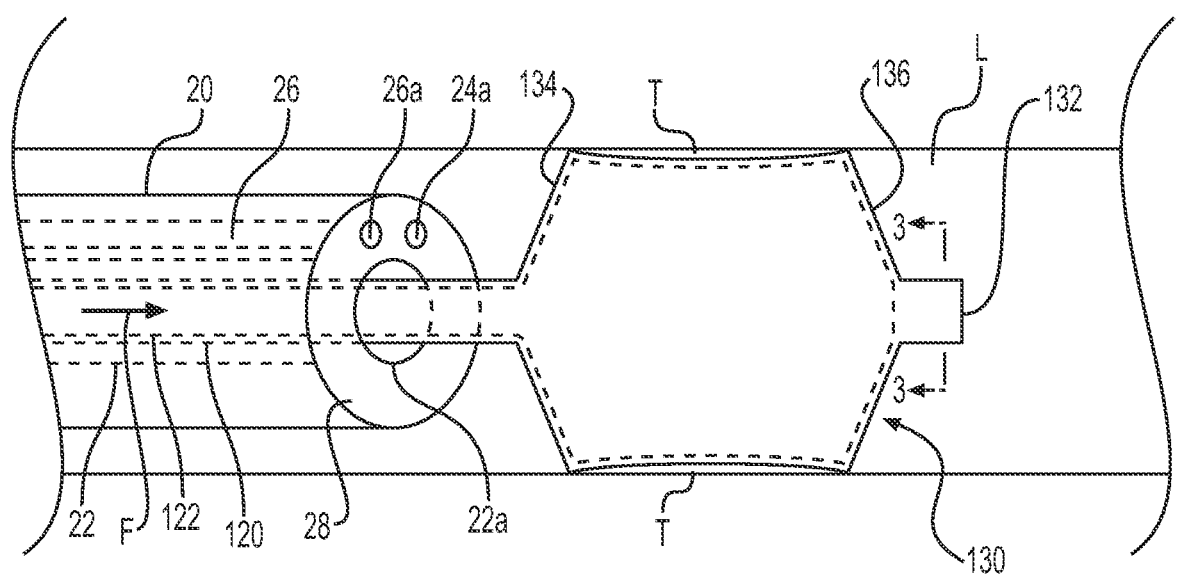
FIG. 3A is a perspective view of a distal end of another medical tool of the medical system of FIG. 1, according to an embodiment.

Referring to FIGS. 1, 2A, and 3A, catheter 20 includes a plurality of lumens, e.g., a first lumen 22, a second lumen (for ease of description, second lumen is not shown, but extends from a proximal end of catheter 20 to an opening 24a shown in FIG. 1), and a third lumen 26 extending from a proximal end of catheter 20 to an opening 26a. According to an example, first lumen 22 is configured to receive sheath 120 of the medical device, as will be described in greater detail herein. First lumen 22 extends from handle 40 and terminates at a first opening 22a at a distal end face 28 of catheter 20. The second lumen and third lumen 26 may receive additional tools, and/or may be used for suction/vacuum, dispensing fluid, imaging, illumination, or the like. For example, distal openings 24a, 26a of the second lumen and third lumen 26 may be open at distal end face 28 of catheter 20. According to an example, fluid may be expelled through one or both of openings 24a, 26a after traveling along the respective second lumen and third lumen 26 from handle 40. Alternatively, debris may be suctioned/vacuumed through one or both of openings 24a, 26a, and/or an electrical fiber may be disposed in one or both of the second lumen and third lumen 26 and attached to a visualization component, such as a camera, or an illumination member, such as a light emitting diode (LED), disposed at openings 24a, 26a. It will be understood that these components may be fixed in openings 24a, 26a, or the components may be extended from distal end face 28 to provide additional illumination of and/or visualization of a target site T. For ease of description, catheter 20 is shown only in FIGS. 1, 2A, and 3A. However, it will be understood that any medical tool described herein may access target site T by being passed through lumen 22 of catheter 20.

With continued reference to FIG. 1, sheath 120 extends within first lumen 22 of catheter 20. Sheath 120 is flexible and has an outer diameter less than an inner diameter of first lumen 22, thereby allowing sheath 120 to slide within and along first lumen 22. Sheath 120 includes an inflatable balloon 130 at a distalmost end. Balloon 130 is actuatable between an open, inflated position and a closed, deflated position using an inflation fluid, e.g., a liquid, such as saline, or a gas, such as $CO_2$. As will be described herein, balloon 130 is capable of being inflated adjacent target site T and distal of a distalmost end of catheter 20, thereby enabling a material, such as a hemostatic or regenerative agent, to be supplied to target site T.

FIG. 2A illustrates catheter 20 disposed in lumen L of a body and adjacent target site T. Sheath 120 is advanced along first lumen 22 by, e.g., pushing on a proximal end of sheath 120, to expose balloon 130 from distal end face 28 of catheter 20. For example, a user may insert balloon 130 into port 44 at handle 40 and advance balloon 130 along lumen 22 by pushing on sheath 120. This movement causes balloon 130 to be exposed from first opening 22a. As described herein, openings 24a, 26a may include lighting and/or visualization elements, which may assist in positioning balloon 130.

Figure 2B:
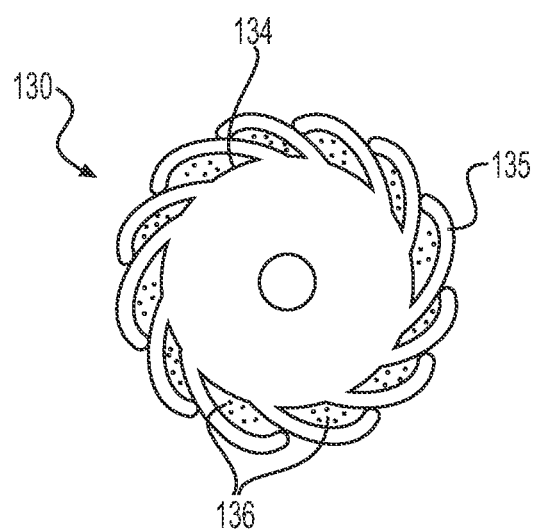
FIG. 2B is a cross-section taken along the line 2-2 of FIG. 2A.

As shown in FIGS. 2A and 2B, target site T protrudes into lumen L. As discussed above, catheter 20 may include actuating elements, e.g., cables, extending from handle 40, to the distal end of catheter 20. Pulling on those cables can bend the end of catheter 20, as necessary, to properly position balloon 130 adjacent target site T. Alternatively, or additionally, a guidewire (not shown) may be advanced adjacent target site T. Sheath 120 may include a central lumen (not shown), and sheath 120 may be advanced along the guidewire.

With continued reference to FIG. 2A, balloon 130 is in a deflated configuration, distal of distal end face 28 of catheter 20 and adjacent target site T. Sheath 120 includes a distal tip 132, and balloon 130 is positioned proximally of distal tip 132. With reference to FIG. 2B, a cross-section along the line 2-2 in FIG. 2A illustrates that balloon 130 has a body 134 that is folded. As will be explained herein, balloon 130 inflates from the deflated configuration by supplying fluid F to balloon 130 via lumen 122.

As further shown in FIG. 2B, body 134 includes folds 135 that create pockets or spaces 136 between adjacent folds 135 in the deflated configuration. Pockets 136 contain material, e.g., a hemostatic or a regenerative agent, that is supplied to target site T, as will be described herein. Balloon 130 may be compliant or non-compliant, and may include any number of folds 135. Each fold 35 may overlie a portion of an adjacent fold 135, to create pockets 136. In other embodiments, adjacent folds 135 do not overlie one another. Each fold 135 also is radially outward of portion of the outer surface of balloon 135 so that they are not part of folds 135, to also create pockets 136. In some examples, folds 135 are the radially outermost portion of balloon 130, e.g., in some examples there is no covering over folds 135 and/or the outermost surface balloon 130. Folds 135 may create pockets 136 for an agent and may extend fully around a circumference of the balloon 130, although in some embodiments, folds 135 may be on only a portion of balloon 130, e.g., folds 135 may only extend partially around the circumference of balloon 130 to target a desired area of tissue for treatment. In some embodiments, different agents may be disposed in different folds 135 around different portions of the balloon 130. For example, some of folds 135 may contain an inactive agent and other folds 135 may contain a catalyst, and the catalyst may activate the inactive agent when balloon 130 is expanded and the inactive agent and the catalyst come into contact. Alternatively, or additionally, various agents may degrade or otherwise become ineffective if exposed to other agents for an extended period of time. Disposing different agents in different folds 135 may improve the lifetime of these agents and may improve the effectiveness of the agents once deployed at target site T.

Figure 3B:
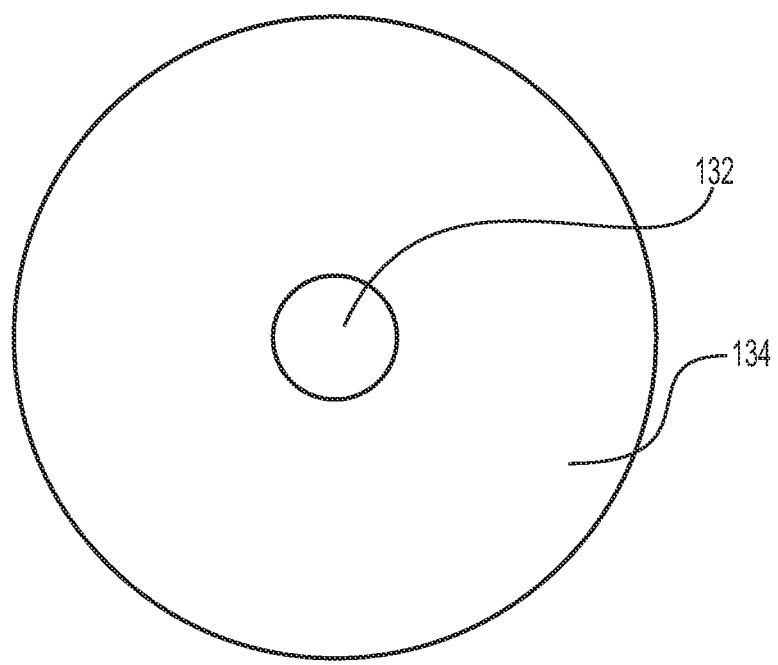
FIG. 3B is a cross-section taken along the line 3-3 of FIG. 3A.

With reference to FIGS. 3A and 3B (which shows a cross-section of balloon 130 along the line 3-3 of FIG. 3A), balloon 130 is shown in the inflated position. According to an example, balloon 130 may be inflated by supplying fluid F, e.g., a gas or a liquid, to lumen 122 of sheath 120 via actuation mechanism 140. For example, one of the first or second channels 123, 124 may be connected to a containment device storing fluid F. Fluid F may travel along lumen 122 and fill balloon 130, causing balloon 130 to inflate. In the inflated or expanded position, body 134 of balloon 130 forms a cylindrical or rounded shape and folds 135 of body 134 and corresponding pockets 136 (see FIG. 2A) partially or completely disappear, exposing the material to target site T (see FIGS. 3A and 3B). During and upon inflation or expansion, the material underlying folds 135 in pockets 136 is released. As shown in FIG. 3A, balloon 130 approaches or abuts against target site T, allowing the material to be transferred to target site T. After the material has been transferred to target site T, balloon 130 is deflated.

An operation of balloon 130 will now be described.

Catheter 20 is inserted into a body through a natural orifice or an incision in a patient. Catheter 20 is advanced along a body lumen to target site T. Once catheter 20 is positioned adjacent target site T, sheath 120 is inserted into port 44 and advanced along first lumen 22. It will be understood that sheath 120 may be inserted into port 44 prior to the beginning of the procedure, e.g., before inserting catheter 20 into the body, and sheath 120 may be advanced to target site T at a same time as catheter 20.

After positioning catheter 20 and sheath 120 adjacent target site T, a proximal end of sheath 120 is manipulated to move sheath 120 along first lumen 22 in a distal direction with respect to catheter 20. Moving sheath 120 in the distal direction forces balloon 130 toward a distal end of catheter 20 and out first opening 22a in distal end face 28, thereby positioning balloon 130 adjacent target site T.

After balloon 130 is positioned outside first lumen 22 and adjacent target site T, balloon 130 is inflated. According to an example, inflating balloon 130 includes attaching one of first or second channels 123, 124 to a fluid containment device and supplying fluid F to lumen 122. Fluid F travels along lumen 122 of sheath 120 to balloon 130. As balloon 130 fills with fluid F, body 134 of balloon 130 inflates or expands, releasing the material within pockets 136 of folds 135. Further inflation or expansion of body 134 forces body 134 toward and against target site T, further causing folds 135 in body 134 to smooth out and press the material against target site T. Fluid F can remain in balloon 130 for a time period, e.g., approximately 10 minutes or less, or approximately one minute or less, sufficient to transfer the material to target site T. This time period may depend on a material of balloon 130 and/or fluid F and an interaction with target site T, and/or a preference of the physician performing the medical procedure. Additionally, the time period may be changed based on when an opening at target site T is closed. According to an example, abutting balloon 130 against target site T and applying pressure to the material may seal a bleed/cut or otherwise close a tear or opening at target site T.

Once the material is sufficiently transferred to target site T or target site T is otherwise treated, balloon 130 is deflated by removing fluid F. For example, to remove fluid F, the other of first or second channels 123, 124 is attached to the fluid containment device and fluid moves, via a syringe or pump operated by a user or an electrically operated pump associated with the fluid containment device, from balloon 130, along the lumen of sheath 120, and into the fluid containment device. Removing fluid F from balloon 130 causes balloon 130 to collapse on itself, and balloon 130 can be removed from the body, e.g., by moving sheath 120 proximally to move balloon 130 into lumen 22 of catheter 20. Alternatively, or additionally, balloon 130 may be moved along a guidewire to remove balloon 130 from the body.

Figure 4A:
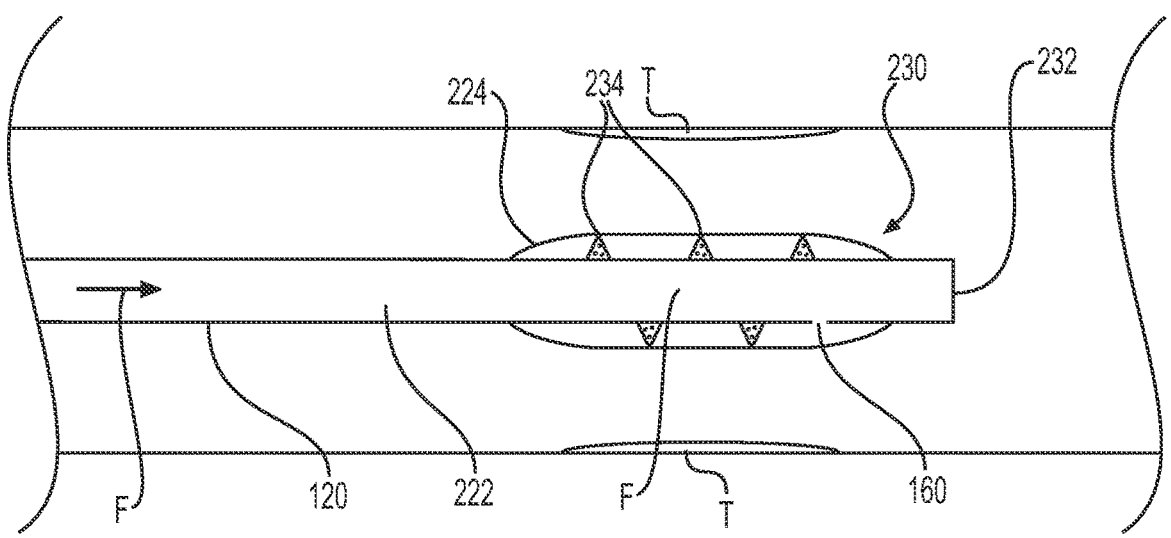
FIGS. 4A-4C are perspective views of a distal end of a medical tool of the medical system of FIG. 1, according to another embodiment.
Figure 4B:
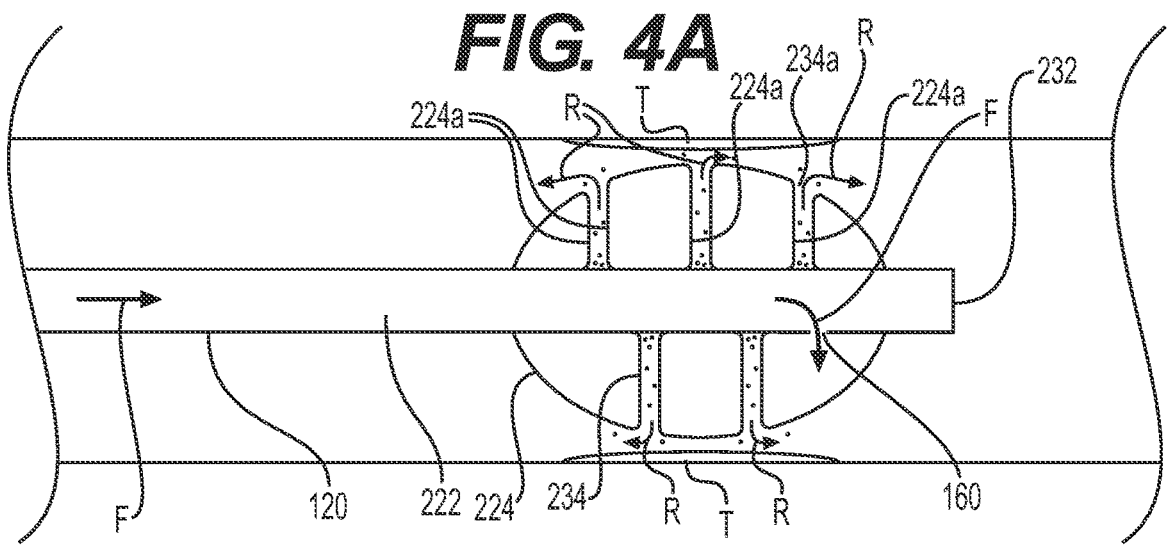
Figure 4C:
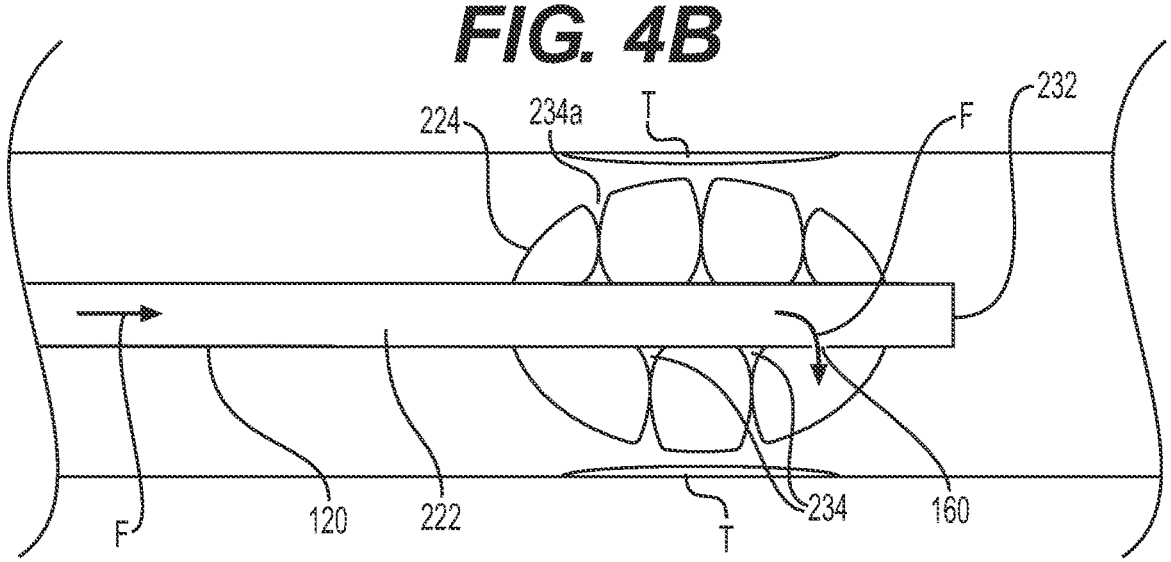

A balloon 230 according to another example is shown in FIGS. 4A-4C. While not shown, balloon 230 may be introduced into a body using a catheter and/or a guidewire, as explained herein. Balloon 230 is proximal of a distal tip 232 of sheath 120, and includes flexible channels 234 that are preloaded with a material, such as a therapeutic or regenerative material described herein. Channels 234 are bounded on sides by exterior surfaces 224a of a body 224 of balloon 230. A radially inner portion of each channel 234 is bounded by an outer surface of sheath 120 (or a surface of balloon 130 fixed to the outer surface of sheath 130). A radially outer portion of each channel 234 defines a channel opening 234a. When balloon 230 is in a deflated orientation, as shown in FIG. 4A, portion of body 224 of balloon 230 overlap channel opening 234a of each of channel 234, containing the material generally to channels 234, although some weeping of material from channels 234 may occur. As balloon 230 is inflated from a deflated configuration by supplying fluid F to balloon 230 via lumen 222, as shown in FIG. 4B, channel openings 234a open (expose to the body lumen), since the portions of body 234 covering channel openings 234a move away from channel openings 234a. This allows the material to flow to target site T from channels 234 via channel openings 234a, as shown by arrows R. For example, fluid F may be supplied along lumen 222 to an opening 160 in lumen 222, e.g., at a distal end thereof, and fluid F may be supplied to balloon 230 via opening 160, thereby causing balloon 230 to inflate. It will be understood that channel openings 234a may be closed in the deflated configuration by any other structure, e.g., a perforated wall of balloon 230 which may rupture once balloon 230 is sufficiently inflated. Perforations or other similar closure mechanisms may be similarly used to selectively close openings described herein.

FIG. 4C shows balloon 230 in a fully inflated configuration, in which the material has been completely or almost completely expelled from channels 234. According to an example, exterior surface 224a that define each of channels 234 may abut each other when in the fully inflated configuration, which aids in expelling a maximum amount of material from each of channels 234. Balloon 230 does not contact target tissue T in FIGS. 4B and 4C. However, it will be understood that balloon 230 may contact and press against target tissue T.

According to an embodiment, channels 234 are generally cylindrical and have a longitudinal axis (at least when inflated) transverse to, and in comes case, generally perpendicular to, a longitudinal axis of sheath 120. However, the orientation and the shape of channels 234 is not limited thereto, and channels 234 may be any orientation, e.g., angled relative to the longitudinal axis, and any shape, e.g., conical, columnar, or cuboidal, sufficient for storing the material and for transferring the material to target site T. Moreover, the number and/or the arrangement of channels 234 is not limited. For example, channels 234 may be equally or randomly spaced along balloon 230. In some examples, an additional curing agent may be supplied along a lumen of sheath 120, separate from lumen 222, and into channels 234, as will be described herein. In other examples, some channels 234 may include a first agent while other while other channels 234 include a second agent, e.g., a curing agent.

An operation of balloon 230 will now be described. Balloon 230 is inserted into the body and advanced to target site T in any manner described herein. Once balloon 230 is adjacent target site T, balloon 230 is inflated in any manner described herein, e.g., by supplying fluid F along lumen 222 to an opening in lumen 222. Since opening 160 is in fluid communication with the balloon 230, balloon 230 begins to inflate, causing body 224 to move and unblock channel openings 234a. As channel openings 234a are covered to open, the material stored in channels 234 is exposed to target site T. The material may be forced from channels 234 via channel openings 234a by a pressure of balloon 230 expanding toward channels 234. As balloon 230 continues to inflate, the material continues to be expelled. Once balloon 130 is fully inflated, surfaces 224a that define each of channels 234 may contact each other, which may assist the material from being expelled from channels 234. After the material has sufficiently coated target site T, balloon 230 is deflated and may be removed from the body, in any manner described herein.

Figure 5A:
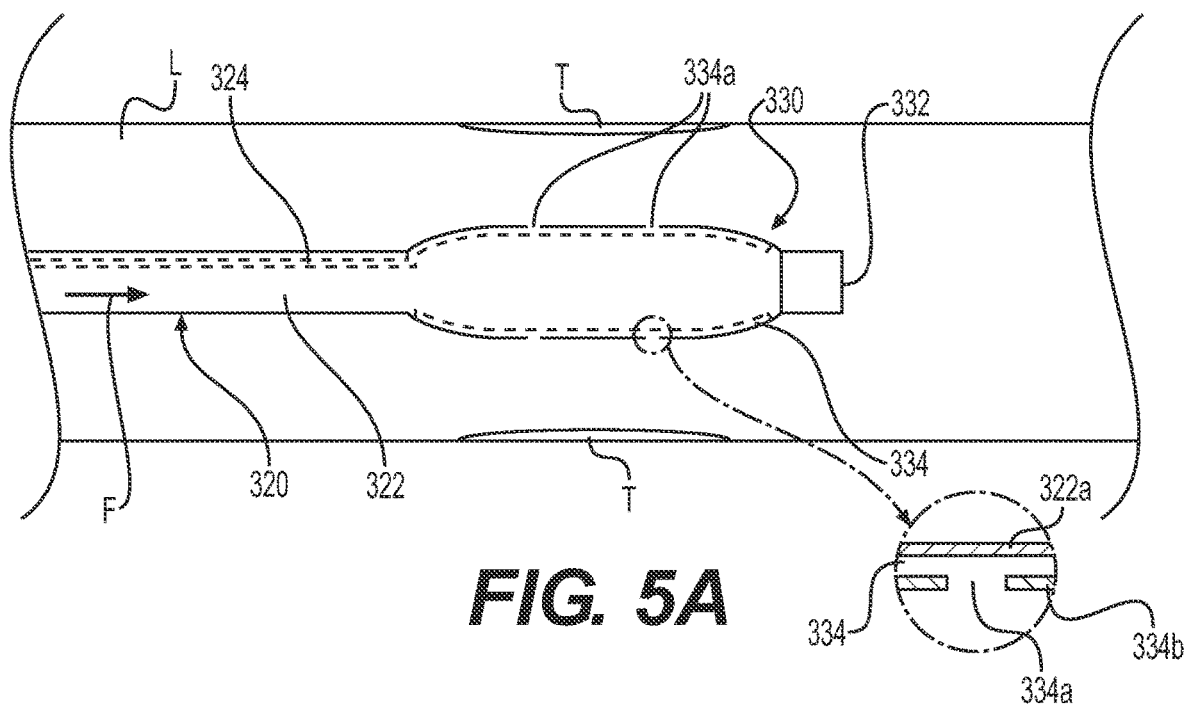
FIGS. 5A and 5B are perspective views of a distal end of a medical tool of the medical system of FIG. 1, according to another embodiment.
Figure 5B:
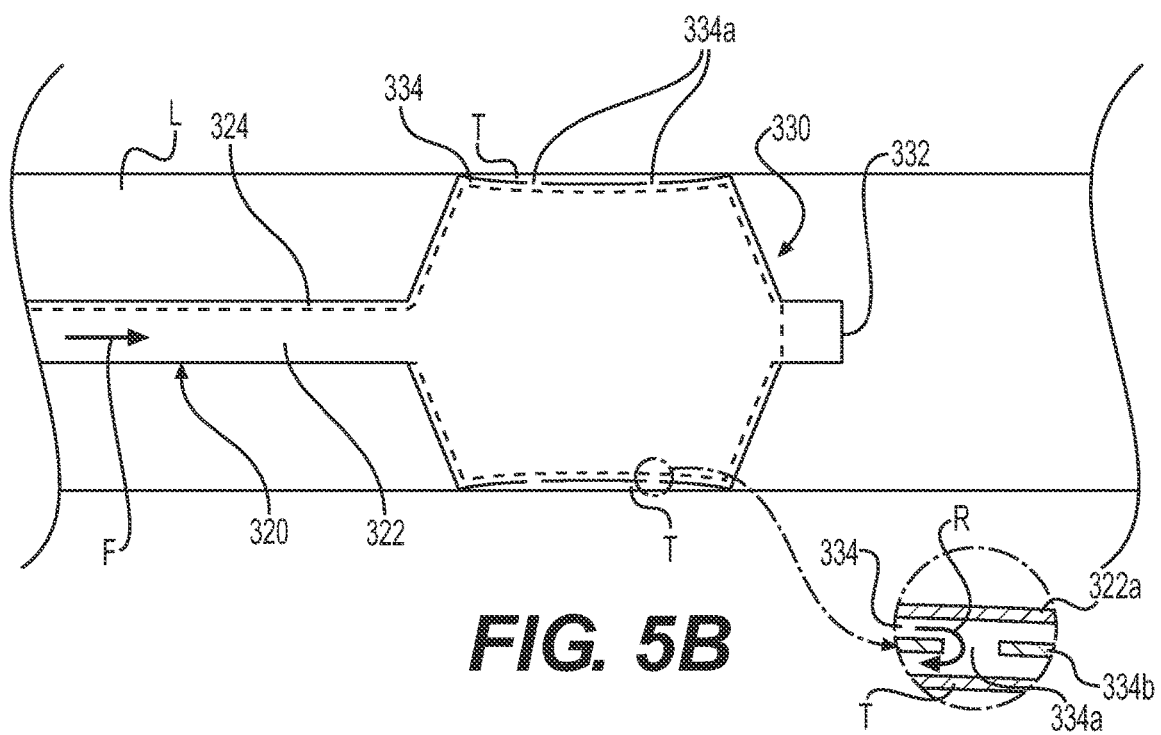

A balloon 330 according to another embodiment is shown in FIGS. 5A and 5B. While not shown, balloon 330 may be introduced into a body using a catheter and/or a guidewire, as explained herein. Balloon 330 is proximal of a distal tip 332 of sheath 320. Sheath 320 includes a first lumen 322 and a second lumen 324, each of which extends from a proximal end of sheath 320 to balloon 330. First lumen 322 receives fluid F from a fluid containment device, as described herein, to inflate balloon 330, as described herein. First lumen 322 also is used for deflation of balloon 330, as described herein. Second lumen 324 is connected to a balloon lumen 334 and receives a material and/or other fluids, e.g., a reagent, an adhesive, air, and/or water, to be supplied to target site T via openings 334a in an exterior surface of balloon 330. Openings 334a are fluidly connected to second lumen 324 via balloon lumen 334. As shown in FIGS. 5A and 5B, balloon lumen 334 is defined by an outer wall 334b of balloon 330 and an inner wall 322a of balloon 330, and balloon lumen 334 is fluidly decoupled from lumen 322 via inner wall 322a. Balloon lumen 334 therefore may be an annular ring-like space or cavity that completely surrounds an inner portion of balloon 330 that receives fluid F. In other embodiments, balloon lumen 334 may only partially surround that inner portion of balloon 330.

According to an example, the material may be preloaded in second lumen 324, and the material may exit openings 334a in outer wall 334b due to a pressure on balloon 330 when balloon 330 inflates. Additionally, or alternatively, a fluid may be supplied along second lumen 324 to force the material through openings 334a and/or by mixing with the material and forcing the mixture from openings 334a. According to another example, the material may be supplied to second lumen 324 after balloon 330 is inflated, e.g., by supplying the material to second lumen 324 using a syringe or other application device. Additionally, a solvent or other material may be supplied to target site T via second lumen 324, before, after, or during delivery of an agent preloaded in balloon lumen 334. The solvent may activate an agent, an adhesive, or the like of the material supplied to target site T. Alternatively, the solvent may be supplied to target site T using a different lumen, as will be described herein.

An operation of balloon 330 will now be described with reference to FIGS. 5A and 5B. Balloon 330 is inserted into the body and advanced to target site T in any manner described herein. Once balloon 330 is adjacent target site T, balloon 330 is inflated in any manner described herein, e.g., by supplying fluid F from a fluid containment device to first lumen 322 to inflate balloon 330. According to an example, balloon lumen 334 is preloaded with a material. As balloon 330 inflates, inner wall 322a of first lumen 322 pushes against the material in balloon lumen 334, supplying the material through openings 334a to target site T. When balloon 330 is sufficiently inflated and is adjacent target site T, the material exits openings 334a, as shown by arrow R, to coat target site T. According to an example, a syringe or other similar device is attached to the proximal end of sheath 320 and may supply solvent to target site T via second lumen 324 after the material is dispensed from openings 334a.

Alternatively, fluid F is first supplied from the fluid containment device to the first lumen 322. Once balloon 330 is properly positioned and sufficiently inflated, material is supplied to target site T via second lumen 324 and openings 334a. For example, a syringe or like device is attached to a proximal end of second lumen 324 and the material is dispensed from the syringe to second lumen 324, and supplied to target site T. According to an example, a second material, e.g., a fluid or solvent, is supplied to second lumen 324 via, e.g., a syringe or like device, after the material is supplied to second lumen 324. The second material may be suitable to move the initially-provided material along second lumen 324 to target site T and/or may provide additional therapeutic properties, e.g., to activate the material. After the material is supplied to target site T, balloon 330 is withdrawn from target site T in any manner described herein.

A balloon 430 according to another example will now be described with reference to FIGS. 6A and 6B. Balloon 430 is similar to any of the balloons described herein, e.g., balloon 430 is attached proximal to a distal end 432 of a sheath 420 and includes a lumen 422 which extends from a proximal end of sheath 420 to balloon 430. Balloon 430 further includes an outer wall 434 which may support a patch 440, as will be described herein. Any other features of any of the other-described balloons may be incorporated into balloon 430.

Figure 6A:
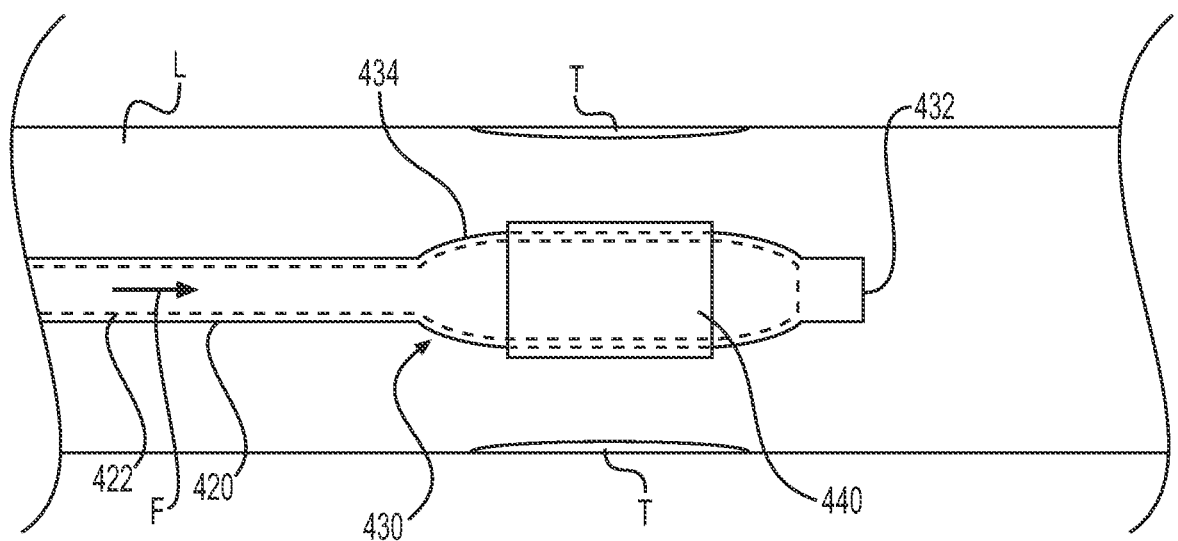
FIGS. 6A and 6B are perspective views of a distal end of a medical tool of the medical system of FIG. 1, according to another embodiment.
Figure 6B:
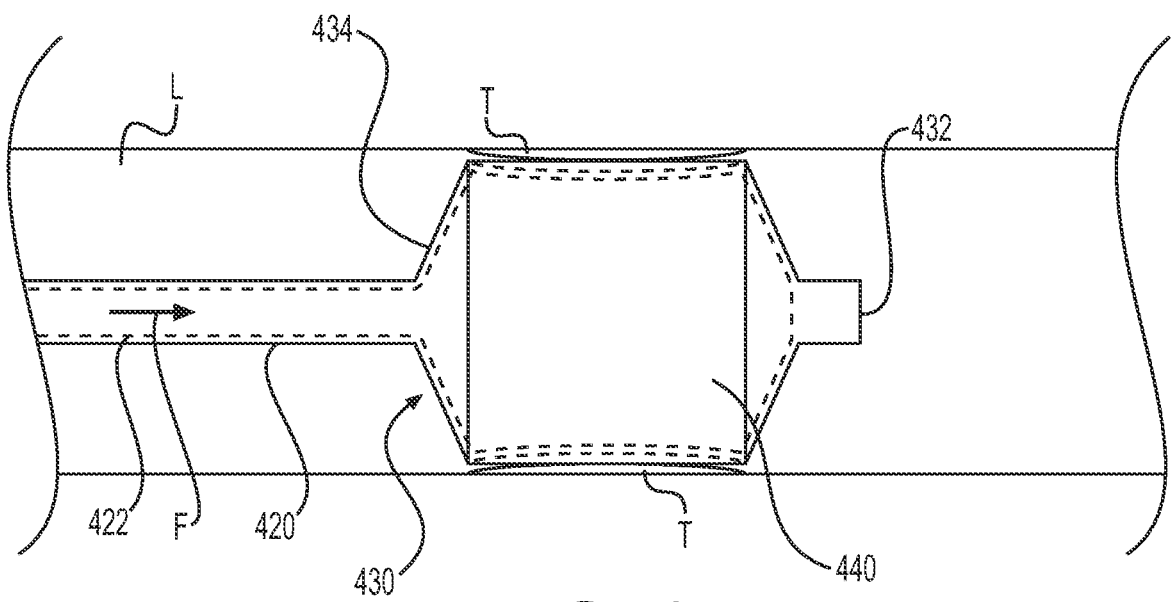

Patch 440 may be formed of a material, e.g., polysaccharides, biodegradable polyurethanes, poly (ethylene oxide) (PEO), poly (ethylene glycol) (PEG), or the like, that allows patch 440 to expand from a low profile, as shown in FIG. 6A, to an expanded profile, as shown in FIG. 6B. An outer surface of patch 440 may include a material, e.g., an adhesive, a reagent, or the like, and is configured to be applied to or attach to target site T to provide a therapeutic or regenerative treatment. According to an example, an inner surface of patch 440 (a surface facing outer wall 434) may also include an adhesive to affix patch 440 to balloon 430 during insertion. As will be explained herein, patch 440 may be removed from balloon 430 after patch 440 is attached to target site T. In some embodiments, a fluid may be supplied by shaft 20 to dissolve the adhesive between patch 440 and balloon 430, while not altering properties of other materials on or in patch 440. While a single patch 440 is shown, it will be understood that balloon 430 may support multiple patches according to the therapeutic need. In addition, while patch 440 may circumscribe all of balloon 430, other embodiments of patches may circumscribe only a portion of balloon 430.

As described herein, balloon 430 is inflated or expanded from the deflated configuration of FIG. 6A to the inflated configuration of FIG. 6B by supplying fluid F from a fluid containment device to balloon 430 via lumen 422. As balloon 430 inflates, patch 440 similarly expands and may be pressed against target site T. Once patch 440 is properly positioned adjacent target site T, patch 440 may adhere to target site T. For example, radiofrequency (RF) electrodes may heat the material on the outer surface of patch 440, curing the adhesive. Alternatively, or additionally, fluid F supplied to balloon 430 to inflate balloon 430 may have a temperature sufficient to heat the material on the outer surface of patch 440 and cure the adhesive. After the material is cured and patch 440 is adhered to target site T, balloon 430 is deflated.

According to another example, an adhesion force between balloon 430 and patch 440 may maintain a position of patch 440 relative to balloon 430 during insertion, and this adhesion force may be overcome after patch 440 is attached to target site T. For example, a cooling fluid (in one example, the cooling fluid may be fluid F) may be supplied to lumen 422 to cool outer surface 434 of balloon 430 and, thus, cool inner surface of patch 440, thereby degrading the adhesive force between balloon 430 and patch 440. Alternatively, or additionally, sheath 420 may be rotated about a central longitudinal axis, causing balloon 430 to rotate with respect to patch 440 and overcome the adhesive force between balloon 430 and patch 440. In yet another example, an agent may be supplied from openings in balloon 430 and patch 440, to degrade the adhesive between balloon 430 and patch 440. The agent may be preloaded in openings in outer surface 434 and/or may be supplied via a separate lumen, according to examples described herein.

An operation of balloon 430 will now be described. Balloon 430 is inserted into the body and advanced to target site T in any manner described herein. Once balloon 430 is positioned adjacent target site T, balloon 430 is inflated in any manner described herein, e.g., by supplying fluid F from a fluid containment device to lumen 422 to inflate balloon 430. As balloon 430 inflates, outer wall 434 pushes against patch 440 and causes patch 440 to expand outward from a central longitudinal axis of balloon 430. When balloon 430 is sufficiently inflated and is adjacent target site T, outer wall 434 pushes or urges patch 440 against target site T. According to an example, an adhesive on an surface of patch 440 facing target site T may already be activated such that patch 440 adheres to target site T when patch 440 contacts target site T. Alternatively, an adhesive material on patch 440 may need to be activated or cured to maintain a position of patch 440 relative to target site T. In this example, an RF transmitter may be placed adjacent target site T, e.g., by being advanced along lumen 422 and into balloon 430. Once the RF transmitter is appropriately positioned, the RF transmitter is activated by, e.g., applying a current to the RF transmitter, thereby generating heat, to activate or cure the adhesive material. Alternatively, fluid F used to inflate or expand balloon 430 may activate the adhesive material on the patch 440, thereby curing the adhesive material to attach patch 440 to target site T.

Once patch 440 is attached to target site 440, balloon 430 is removed from target site T. According to a first example, balloon 430 is deflated by removing fluid F from balloon 430, as described herein. Alternatively, a user may first rotate sheath 420, thereby causing balloon 430 to rotate and release patch 440 from balloon 430. For example, in the event patch 440 uses an adhesive to maintain a position relative to balloon 430 during insertion to target site T, rotating sheath 420 may generate a force sufficient to overcome the adhesion force between balloon 430 and patch 440. Alternatively, or additionally, a reagent may be supplied from the proximal end of sheath 420 to balloon 430. The reagent may be supplied to an outer surface of outer wall 434 to counteract the adhesive forces between balloon 430 and patch 440. After patch 440 is detached from balloon 430, balloon 430 is deflated and may be withdrawn into a catheter, e.g., catheter 20 shown in FIG. 1, to remove balloon 430 from the body.

Figure 7A:
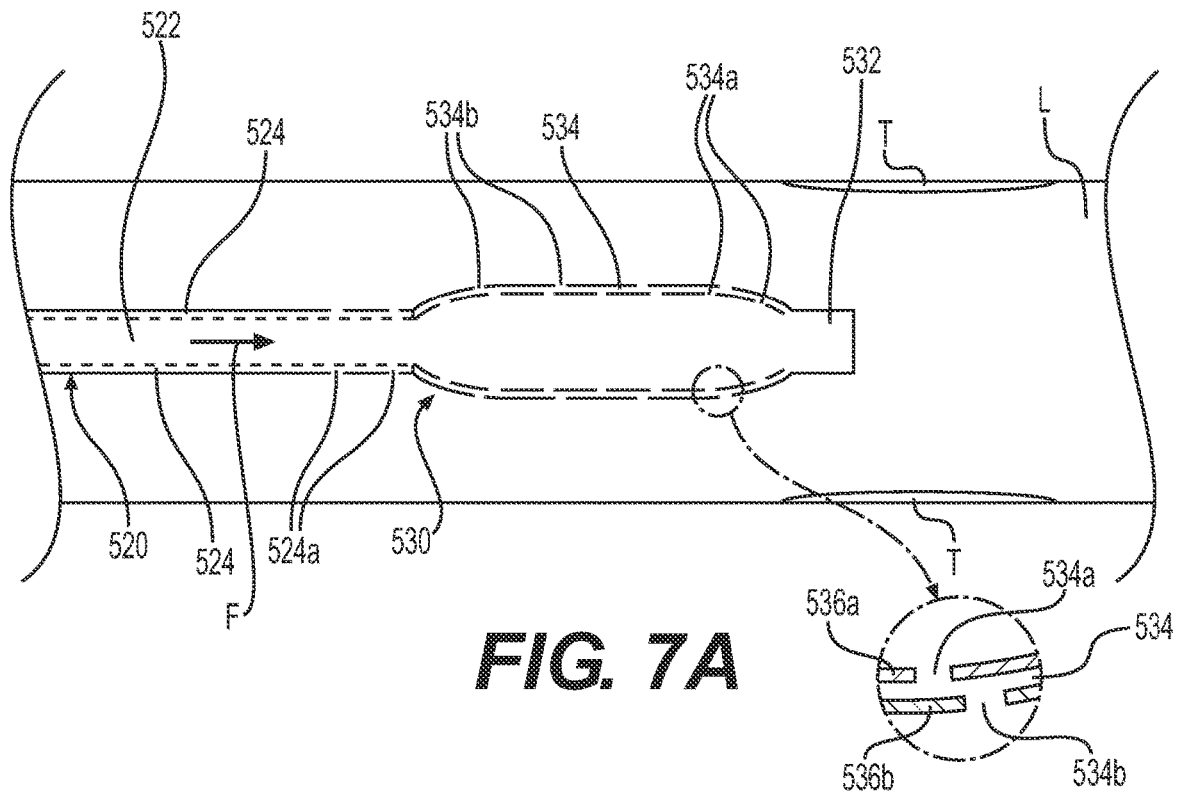
FIGS. 7A and 7B are perspective views of a distal end of a medical tool of the medical system of FIG. 1, according to yet another embodiment.
Figure 7B:
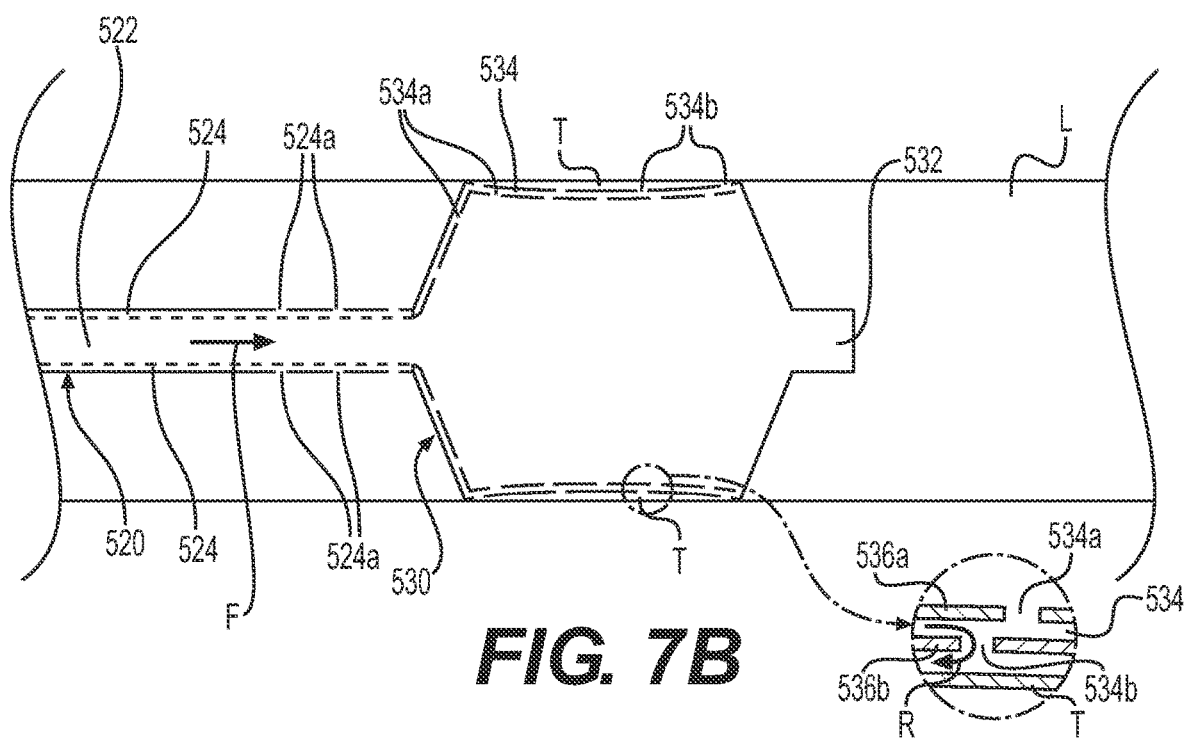

A balloon 530 according to another example will be described with reference to FIGS. 7A and 7B. Balloon 530 is similar to any of the balloons described herein, e.g., balloon 530 is attached proximal to a distal tip 532 of a sheath 520 and includes a lumen 522 which extends from a proximal end of sheath 520 to balloon 530. An inner wall 536a of balloon 530 includes a plurality of first openings 534a that are fluidly coupled with second openings 534b in an outer wall of balloon 530. A balloon lumen 534 is defined by inner wall 536a and outer wall 536b of balloon 530, and is fluidly coupled to openings 534a in inner wall 536a and openings 534b in outer wall 536b. A sheath lumen 524 extends from a proximal end of sheath 520 and terminates proximal to balloon 530. Sheath lumen 524 communicates with a plurality of third openings 524a in outer wall of sheath 520, which will be described in greater detail herein.

As described herein, fluid F is supplied along lumen 522 from a proximal end of sheath 520 to balloon 530 to inflate or expand balloon 530. According to an example, fluid F may include a solvent, such as a solvent having an acidic pH level of approximately 3-5, or a pH of approximately 4. As fluid F is supplied to balloon 530, balloon 530 inflates or expands adjacent target site T, as shown in FIG. 7B. A material, such as a therapeutic material or the like described herein, may be disposed (preloaded) within balloon lumen 534 in a powder or viscous fluid form. As balloon 530 inflates or expands, fluid F may pass from lumen 522, through openings 534a, and into lumen 534, mixing with the material. This mixture is supplied via openings 534b to target site T. In some embodiments, an additional material or fluid, e.g., a curing agent, may be supplied to sheath lumen 524 and may be supplied to target site from sheath lumen 524 via openings 524a. That curing agent, or other fluid, may be supplied before, during, or after delivery of the material to target site T.

An operation of balloon 530 will now be described. Balloon 530 is inserted into the body and advanced to target site T in any manner described herein. Once balloon 530 is positioned adjacent target site T, balloon 530 is inflated in any manner described herein, e.g., by supplying fluid F from a fluid containment device to lumen 522 to inflate balloon 530. As balloon 530 inflates, an outer surface of balloon 530 approaches and/or abuts against target site T. During inflation, or just subsequent to inflation, fluid F passes from lumen 522 and within balloon 530 into balloon lumen 534 via openings 534a. Fluid F mixes with material disposed within balloon lumen 534, reducing the viscosity of the material and/or dissolving the material into a solution including the material and fluid F. The solution of material and fluid is subsequently supplied to target site T via openings 534b. Alternatively, a pressure may be exerted by fluid F on the material in balloon lumen 534 and force the material from balloon lumen 534 to target site T via openings 534b.

After the mixture, including fluid F from lumen 522 and the material from balloon lumen 534, coats target site T, a second material, e.g., an activation fluid, may be supplied from a proximal end of sheath 520 to sheath lumen 524. The second material or the second fluid may travel along sheath lumen 524 and be supplied to target site T via openings 524a. It will be understood that balloon 530 may be deflated before, during, or after supplying the second material from openings 524a. For example, the second material or the second fluid may be guided to target site T by a shape of a proximal end of balloon 530, e.g., a sloping surface of balloon 530. After the second fluid is supplied to target site T, balloon 530 is deflated and removed from the body in any manner described herein.

It will be apparent to those skilled in the art that various modifications and variations can be made to the disclosed device without departing from the scope of the disclosure. For example, any material or fluid may be contained in lumens or otherwise supplied to and/or from a balloon to be expelled from the application device to a target location, including but not limited to materials having therapeutic effects. Additionally, or alternatively, unless otherwise specified, the medical device described herein may be formed of any metal, alloy, plastic, or ceramic, or any combination thereof, suitable for use in medical applications. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    a sheath having a proximal end, a distal end, and at least one lumen extending from the proximal end to the distal end; and
    only one balloon at the distal end of the sheath and having an inflated configuration and a deflated configuration,
    wherein the only one balloon defines (1) only one balloon lumen both radially inward of an exterior surface of the only one balloon and configured to retain a first material for delivery of the first material onto a target site, and (2) a space in fluid communication with the at least one lumen of the sheath,
    wherein the at least one lumen includes a sheath lumen,
    wherein the medical device is configured to be attached to a fluid containment device,
    wherein a fluid from the fluid containment device is configured to be supplied to the sheath lumen to transition the only one balloon from the deflated configuration to the inflated configuration,
    wherein the only one balloon lumen is disposed within an inner wall and an outer wall of the only one balloon,
    wherein the only one balloon lumen only partially circumferentially surrounds the space of the only one balloon, and
    wherein the only one balloon includes a plurality of openings in the outer wall of the only one balloon fluidly coupled to the only one balloon lumen.

2. The medical device according to claim 1, wherein the only one balloon does not include an outer coating of the first material in the deflated configuration.

3. The medical device of claim 1, wherein the sheath is attached to a distal end of an actuating device.

4. The medical device of claim 3, wherein the actuating device is a Y-shaped member including a first channel and a second channel.

5. The medical device of claim 4, wherein a fluid travels through the first channel, inflating the only one balloon, wherein the fluid travels out of the only one balloon through the second channel, deflating the only one balloon.

6. The medical device of claim 5, wherein the fluid containment device is configured to contain the fluid, the first channel is attachable to the fluid containment device, and the fluid travels from the fluid containment device through the first channel into the only one balloon, inflating the only one balloon;
    wherein the second channel is attachable to the fluid containment device and the fluid travels from the only one balloon through the second channel into the fluid containment device, deflating the only one balloon.

7. The medical device of claim 6, further comprising a catheter configured to contain the only one balloon and the sheath within a first opening, the catheter including a distal end face, the distal end face including a second opening and a third opening each fluidly connected to a lumen, wherein the second opening may supply fluid and the third opening may supply suction.

8. The medical device of claim 1, wherein the only one balloon lumen is configured to deliver the first material and a second material; wherein delivery of the second material forces remaining amounts of the first material within the only one balloon lumen onto the target site in a body.

9. The medical device of claim 8, wherein the second material is a different material from the first material, wherein the second material is configured to activate the first material.

10. The medical device of claim 9, wherein a distal end of the only one balloon abuts a proximal end of a distal tip of the sheath.

11. The medical device of claim 8, wherein the first material is an adhesive, and the second material is a solvent or a fluid configured to activate the first material.

12. The medical device of claim 1, wherein a portion of the only one balloon lumen extends from a proximal end of the only one balloon and terminates prior to a distal tip of the sheath.

13. A medical device, comprising:
    a shaft having a distal end;
    a handle at a proximal end of the shaft, the shaft including a first lumen and a second lumen each with an opening at the distal end of the shaft, the opening of the first lumen configured to deliver fluid or suction;
    the second lumen including:
        a sheath having a proximal end, a distal end, and at least one lumen extending from the proximal end of the sheath to the distal end of the sheath; and
        only one balloon at the distal end of the sheath and having an inflated configuration and a deflated configuration;
    a first agent; and
    a second agent different from the first agent and configured to activate the first agent;
    wherein the only one balloon includes (1) a balloon lumen both radially inward of an exterior surface of the only one balloon and configured to retain the first agent for delivery of the first agent onto a target site, and (2) a space in fluid communication with the at least one lumen of the sheath,
    wherein the at least one lumen of the sheath includes a sheath lumen, wherein the medical device is configured to be attached to a fluid containment device, wherein a fluid from the fluid containment device is configured to be supplied to the sheath lumen to transition the only one balloon from the deflated configuration to the inflated configuration, wherein the balloon lumen is disposed within an inner wall and an outer wall of the only one balloon, wherein the balloon lumen only partially circumferentially surrounds the space of the only one balloon, wherein the only one balloon includes a plurality of openings in the outer wall of the only one balloon fluidly coupled to the balloon lumen, and wherein the balloon lumen is configured to deliver the first agent and the second agent; wherein delivery of the second agent forces remaining amounts of the first agent within the balloon lumen onto the target site.

14. The medical device of claim 13, wherein a portion of the balloon lumen extends from a proximal end of the only one balloon and terminates prior to a distal tip of the sheath.

15. The medical device of claim 13, wherein the first agent includes an adhesive, and the second agent includes a solvent or a fluid.

16. The medical device of claim 13, wherein the first agent includes an adhesive, and the second agent includes an adhesive.

17. The medical device of claim 13, wherein the first agent is preloaded in the balloon lumen and includes an adhesive; wherein the second agent is supplied to the balloon lumen via a syringe; and wherein the second agent includes a solvent or a fluid.

* * * * *